United States Patent [19]

Della Valle et al.

[11] Patent Number: 5,260,464

[45] Date of Patent: Nov. 9, 1993

[54] CARNITURE DERIVATIVES, PROCESS FOR THEIR PREPARATION, AND THEIR USE IN HUMAN THERAPY

[75] Inventors: Francesco Della Valle, Padua; Aurelio Romeo, Rome, both of Italy

[73] Assignee: Fidia S.p.A., Italy

[21] Appl. No.: 518,417

[22] Filed: May 3, 1990

[30] Foreign Application Priority Data

May 3, 1989 [IT] Italy .................. 20359 A/89

[51] Int. Cl.$^5$ .............................................. C07F 9/02
[52] U.S. Cl. ........................................ 554/80; 554/79
[58] Field of Search ................ 260/403; 554/79, 80; 514/78, 77

[56] References Cited

U.S. PATENT DOCUMENTS 5,008,288  4/1991  Stracher et al. ................ 514/2

OTHER PUBLICATIONS

Chemical Abstracts, vol. 82, #21, 1985, p, 134462d.
Eibl et al., Biochemica et Biophysica Acta, vol. 553, pp. 476–488, 1979.

Primary Examiner—José G. Dees
Assistant Examiner—Deborah D. Carr
Attorney, Agent, or Firm—Birch, Stewart, Kolasch & Birch

[57] ABSTRACT

New carnitine derivatives are described having the formula (I):

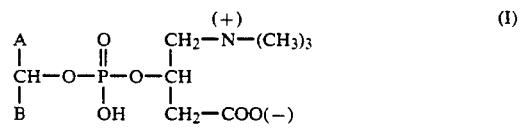

wherein $A = H$, $-(CH_2)_n-O-CO-R_1$, n being 1 or 2, and $B = -(CH_2)_m-O-CO-R_2$, m being 1, 2, 3, or 4 with the limitation that when $A = -(CH_2)_n-O-CO-R_1$, m is 1 or 2, and in which $R_1$ and $R_2$, equal or different are radicals of aliphatic, aromatic, araliphatic, alicyclic or heterocyclic acids.

The process for preparing said derivatives is also described and their use in the therapy of human pathologies associated with neuronal damages.

5 Claims, 4 Drawing Sheets

CARNITURE DERIVATIVES, PROCESS FOR THEIR PREPARATION, AND THEIR USE IN HUMAN THERAPY

The present invention refers to new carnitine derivatives of formula (I):

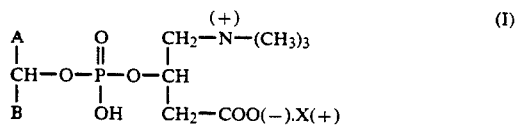

in which A=H, —(CH$_2$)$_n$—O—CO—R$_1$, n being 1 or 2, and B=—(CH$_2$)$_m$—O—CO—R$_2$, m being 1, 2, 3 or 4, with the limitation that when A=—(CH$_2$)$_n$—O—CO—R$_1$, m=1 or 2, and in which R$_1$ and R$_2$, equal or different, are radicals of aliphatic, aromatic, araliphatic, alicyclic or heterocyclic acids, R$_1$ and R$_2$ being preferably radicals of saturated, mono- or polyunsaturated aliphatic acids with a maximum of 20 carbon atoms as, for instance, formic, acetic, propionic, butyric, valerianic, capronic, caprinic, lauric, myristic, palmitic, palmitoleic, stearic, oleic, linoleic, linolenic, arachidonic acid; they may also be radicals of hydroxy acids such as lactic acid, amino-acids, such as glycine, or bicarboxylic acids, such as succinic, glutaric, malonic or maleic acid. When R$_1$ and R$_2$ are aromatic acid radicals. The preferred acids are the ones with only one benzene ring, in particular benzoic acid and its derivatives having as ring substituents methyl, hydroxy, amino or carboxy groups, such as p-aminobenzoic acid, salicylic acid or phthalic acid.

X may be an alkali or earth alkali metal, a primary, secondary, tertiary amine or a quaternary ammonium, aliphatic, aromatic or heterocyclic base.

X is preferably potassium, sodium, ammonium, calcium, magnesium, piperazine, proglycamine (3-amino-1,2-dihydroxy propane), lysine, meglumine (N-methyl glucamine), betaine, choline, aminobutanol, ethanolamine, arginine, carnitine, diethanolamine, dimethylamino ethanol, dimethyl piperazine.

The present invention also refers to a process for preparing the new carnitine derivatives, and their use in the therapy of human diseases associated with neuronal damages.

Numerous carnitine derivatives are known, in particular the acyl derivatives which are described in many patents and articles. Phospholipidic carnitine derivatives are also known. However, carnitine derivatives of general formula (I) have never been described.

We now have found new carnitine derivatives of general formula (I):

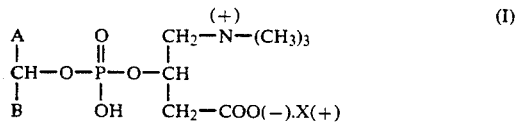

in which A=H, —(CH$_2$)$_n$—O—CO—R$_1$, n being 1 or 2, and B=—(CH$_2$)$_m$—O—CO—R$_2$, m being 1, 2, 3, 4, with the limitation that when A=—(CH$_2$)$_n$O—CO—R$_1$, m=1 or 2, and in which R$_1$ and R$_2$, equal or different, are radicals of aliphatic, aromatic, araliphatic, alicyclic or heterocyclic acids, R$_1$ and R$_2$ being preferably radicals of saturated, mono- or polyunsaturated aliphatic acids with a maximum of 20 carbon atoms as, for instance, formic, acetic, propionic, butyric, valerianic, capronic, caprinic, lauric, myristic, palmitic, palmitoleic, stearic, oleic, linoleic, linolenic, arachidonic acid; they may also be radicals of hydroxy acids, such as lactic acid, amino-acids, such as glycine, or bicarboxylic acids, such as succinic, glutaric, malonic or maleic acid. When R$_1$ and R$_2$ are aromatic acid radicals, the preferred acids are the ones with only one benzene ring, in particular benzoic acid and its derivatives having as ring substituents methyl, hydroxy, amino or carboxy groups, such as p- aminobenzoic acid, salicylic acid or phthalic acid.

X may be an alkali or earth alkali metal, a primary, secondary, tertiary amine or a quaternary ammonium, aliphatic, aromatic or heterocyclic base.

X is preferably potassium, sodium, ammonium, calcium, magnesium, piperazine, proglycamine (3-amino-1,2-dihydroxy propane), lysine, meglumine (N-methyl glucamine), betaine, choline, aminobutanol, ethanolamine, arginine, carnitine, diethanolamine, dimethylamino ethanol, dimethyl piperazine.

The new derivatives according to the present invention are active in the therapy of human diseases associated with neuronal damages. The new carnitine derivatives according to the present invention were obtained employing a new synthesis process described below.

Figure 1A:
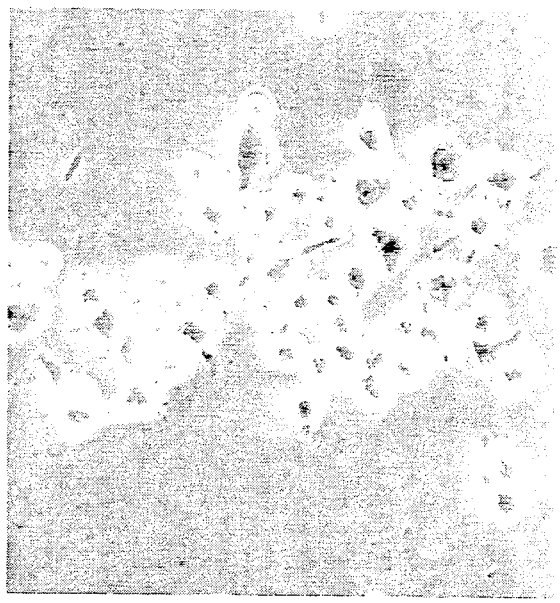
FIG. 1a shows a control cell group of neuroblastoma cells.

GENERAL PROCESS OUTLINE a) A phosphoric acid derivative of formula (II) wherein A=H, —(CH$_2$)$_n$—O—CO—R$_1$, n being 1 or 2, and B=—(CH$_2$)$_m$—O—CO—R$_2$, m being 1, 2, 3, 4, with the limitation that when A=—(CH$_2$)$_n$—O—CO—R$_1$, m=1 or 2 and in which R$_1$ and R$_2$, equal or different, are radicals of aliphatic, aromatic, araliphatic, alicyclic or heterocyclic acids and Z=H or OH.

A simple L-carnitine salt (III) and a suitable condensing agent are dissolved in a suitable organic solvent;

b) the thus obtained solution is heated to evaporate the solvent;

c) the residue is taken up with another suitable organic solvent and purified;

d) the purified product is dissolved in a suitable organic solvent and hydrogenated in the presence of a hydrogenation catalyst; when Z=H, phase d) is modified thus:

the purified fraction is dissolved in a suitable organic solvent and oxidized with a suitable oxidizing agent, the preferred oxidizing agent being iodine in watery pyridine;

e) the solution is purified and concentrated until a precipitate is formed which is separated and dried, obtaining a compound of formula (I)

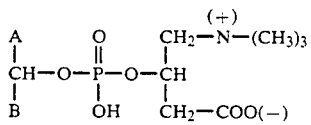

In the general above described process outline the preferred conditions are:

in stage a): the organic solvents may be selected among the tertiary organic bases, preferably pyridine and quinoline;

in stage b): the solution is first heated for about 1 hour at a temperature of between approximately 40° and 80° C. under stirring; the solution is then kept at room temperature for a time approximately comprised between 2 and 3 hours;

in stage c): the residue is dried under reduced pressure and then taken up with ethyl or isopropyl ether, the precipitate is filtered off, the ether solution is evaporated and the residue taken up with a solvent selected among the chlorinated organic solvents, such as chloroform, methylene chloride, dichloroethane, and charged in a chromatographic column which is eluted with an aqueous-alcoholic solvent, such as a mixture of methanol and water;

in stage d): the preferred solvent is acetic acid and the hydrogenation is performed with the aid of palladium on carbon catalyst;

in stage e): the solution is filtered on celite or other similar filter aid and evaporated under reduced pressure.

Of the new carnitine derivatives according to the present invention, salts were prepared with metals and with organic bases, according to conventional methods.

Among the metal and organic bases salts are to be mentioned particularly the ones that can be employed therapeutically, such as the alkali and earth alkali metal salts, for instance the potassium, sodium, ammonium, calcium, magnesium salts, and also the salts with organic bases for instance with primary, secondary, or tertiary amines or with aliphatic or aromatic or heterocyclic quaternary ammonium bases, such as piperazine, proglycamine (3-amino-1,2-dihydroxy propane), lysine, meglumine (N-methyl glucamine), betaine, choline, aminobutanol, ethanolamine, arginine, carnitine, diethanolamine, dimethylamino ethanol, dimethyl piperazine.

For the purpose of demonstrating the therapeutic activity of the new carnitine derivatives according to the present invention, tests were made in vivo and in vitro employing some of the new carnitine derivatives synthetized as described supra.

The results acquired in the last ten years show that nervous cells, both in vitro and in vivo may undergo morphological and functional modifications in answer to intrinsic and extrinsic modifications of their microenvironment. This property, which may be designated as neuroplasticity, was shown to be necessary for the manifestation of reparative processes following a neuronal damage. The evaluation of the effectiveness of the new activ principles in facilitating neuroplasticity processes, and thus in improving the neurological results following a neuronal damage in man, is fundametally based on the use of neuronal cultures.

For these evaluation is fundamental the use of neuronal cultures as the processes involved in the neuroplasticity phenomenon control the morphological and/or functional modifications (for example the neuritic growth) of these cells.

Agents which are effective in inducing or facilitating neuritic growth in vitro are also agents apt to facilitate the manifestation of neuroplasticity.

In order to demonstrate the activity of the new carnitine derivatives according to the present invention, they were experimented in vitro with a highly significant test.

For illustrative purposes, we report below a detailed description of the experiments performed with a product according to the present invention.

TEST 1

The biological activity of the carnitine derivatives according to the present invention, both in the racemic (D,L) and in the optically active L form, obtained following the above described process, was tested in comparison with the one of acetyl-L-carnitine, on mice neuroblastoma C 1300, Neuro-2a clone cells obtained from the American Cell Type Culture Collection (Bethesda, Md.) and on control cells. The acetyl-L-carnitine was selected as comparison substance because its activity in the therapy of peripheral neuropathies was described, e.g. in the Italian patent 1196564 filed Aug. 4, 1986.

Neuroblastoma neuron cultures may, under suitable conditions, express various functions which are characteristic of mature neurons, and allow furthermore qualitative and quantitative evaluations of the biochemical parameters which may be correlated with the different development stages (Denis-Donini D; Augusti-Tocco G; (1980): Molecular and lectin probe analysis of neuronal differentiation; in Moscona, Monroy, Neuronal Development in model system p.p. 323-348 (Academic Press, New York).

MATERIALS AND METHODS a) Solutions Employed

The new carnitine derivatives were dissolved at the concentration of 10 mg/ml TRIS/HCL 5 nM pH 7.8, sonicated for 2 minutes, then filtered on Acrodisc Filter 45 um (Gelman) and diluted to a final concentration of $1 \times 10^{-4}$M with a culture medium containing Dulbecco's modified Eagle medium (Dmem, Flow), 10% bovine fetal serum (Fcs, Lot 2 A02 Seromed), penicillin (100 units/ml, Irvine) and L-glutamine (2 mM, Sigma). Acetyl-L-carnitine was dissolved directly in the above described medium, filtered and then diluted with further medium to obtain final concentrations of:

$1 \times 10^{-2}$M, $5 \times 10^{-3}$M, $1 \times 10^{-3}$M, $5 \times 10^{-4}$M, $1 \times 10^{-4}$M, $5 \times 10^{-5}$M.

b) EMPLOYED CULTURES, MODES OF PREPARATION INCUBATION, ANALYTICAL METHODS

The $N_2A$ cell were plated at a density of 10,000 cells/well (24-costar) in the described culture medium. After 24 hours on the plate the medium was exchanged with 350 ul fresh medium, with and without the products and left for 24 hours for the morphological evalutation (% cells with neurites) or 48 hours for the dosage of the incorporation in DNA of methyl [$^3$-H] thymidine ($^3$H Tdr, Amersham) (Leon A.; Facci L.; Benvegnù D.; Toffano G.; (1982): Morphological and biochemical effect of ganglioside in neuroblastoma cells. Dev. Neurosci. 5; 108-114) and for the count of the vital cells by colorimetry (D.O.=570-630) with 3-(4,5-dimethyl-thiazol-2-yl)-2,5-diphenyl-tetrazolium (MTT); the dye colors only the vital cells (maximum value 100=yellow color) (Mosmann T.; (1983): Rapid colorimetric assay for cellular growth and survival: Application to Proliferation Cytotoxicity Assay. J. Immunol. Methods 65: 55-63).

RESULTS

Figure 1B:
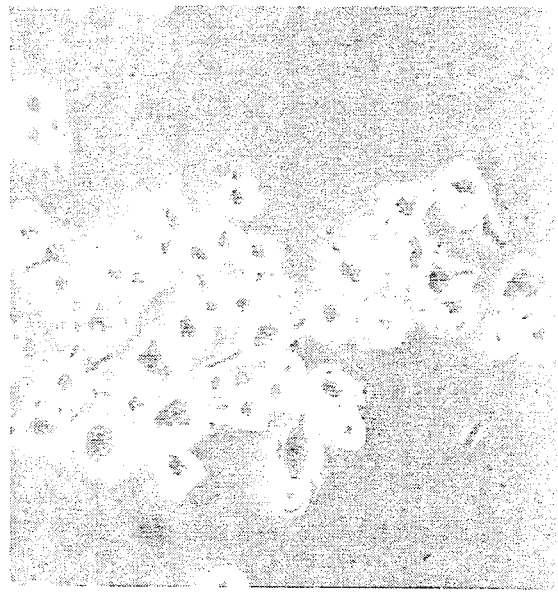
FIG. 1b shows that acetyl-L-carnitine was found to be totally inactive in inducing morphological differentiation in neuroblastoma N$_2$A cells in the various concentrations employed.
Figure 1E:
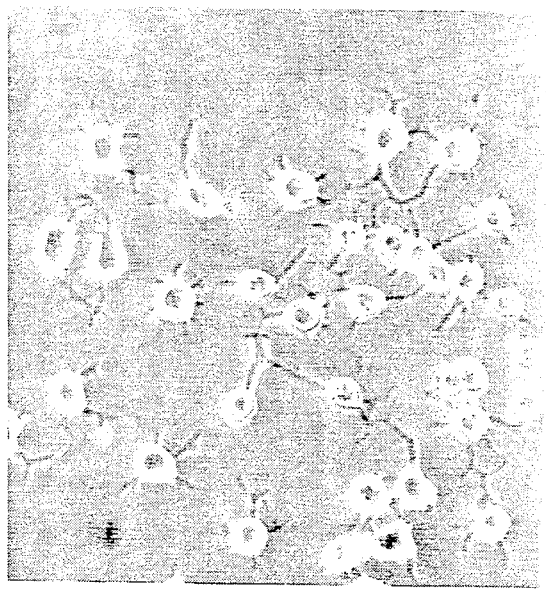
FIG. 1e shows that the new carnitine derivatives were found to be active in inducing morphological differentiation in neuroblastoma N$_2$A cells when employed in racemic form at a concentration of $10^{-4}$M.
Figure 1F:
FIG. 1f shows that the new carnitine derivatives were found to be active in inducing morphological differentiation in neuroblastoma N$_2$A cells when employed in L form at a concentration of $10^{-4}$M.

The new carnitine derivatives were found to be active in inducing a morphological differentiation in neuroblastoma $N_2A$ cells, both when the employed in the racemic (FIG. 1e) and in the L form (FIG. 1f) at the concentration of $10^{-4}M$; on the contrary, acetyl-L-carnitine was found to be totally inactive in the various concentrations employed (FIG. 1b). The control cell group is reported in FIG. 1a.

Table III reports the results:

TABLE III

| concentr. | % cells with neurites | $^3$H Tdr dpm/2h/well | MTT D.O. = 570-630 | $^3$H Tdr/MTT |
|---|---|---|---|---|
| Control | | | | |
|  | 5 | 55271 ± 2540 | 0.353 ± 0.011 | 157 × 10$^3$ |
| Acetyl-L-carnitine | | | | |
| 1 × 10$^{-2}$M | 5 | 51374 ± 5001 | 0.313 ± 0.010 | 165 × 10$^3$ |
| 5 × 10$^{-3}$M | 5 | 49637 ± 1153 | 0.286 ± 0.015 | 173 × 10$^3$ |
| 1 × 10$^{-3}$M | 5 | 49835 ± 4076 | 0.347 ± 0.012 | 144 × 10$^3$ |
| 5 × 10$^{-4}$M | 5 | 53634 ± 1825 | 0.334 ± 0.010 | 161 × 10$^3$ |
| 1 × 10$^{-4}$M | 5 | 51014 ± 2125 | 0.336 ± 0.010 | 152 × 10$^3$ |
| 1 × 10$^{-5}$M | 5 | 46255 ± 6047 | 0.361 ± 0.008 | 128 × 10$^3$ |
| 1,3-dipalmitoylglycero-2-phospho-D,L-carnitine | | | | |
| 1 × 10$^{-4}$M | 55 | 36568 ± 766 | 0.233 ± 0.015 | 157 × 10$^3$ |
| 1,3-dipalmitoylglycero-2-phospho-L-carnitine | | | | |
| 1 × 10$^{-4}$M | 29 | 32204 ± 1291 | 0.227 ± 0.016 | 142 × 10$^3$ |

As proved from the data reported in the table, the new carnitine derivatives proved to be active in reducing the $^3$H Tdr incorporation in DNA (index of lower proliferation, hence of higher cellular differentiation) while no effect resulted when employing acetyl-L-carnitine. The colorimetric MTT dosage puts in evidence the lack of any toxic effect of the tested compounds.

For purely illustrative purposes, we report hereinbelow some examples of the preparation of the new derivatives, performed according to the described general outline.

EXAMPLE 1

1,3-dipalmitoyl-glycero-2-phospho-D,L-carnitine 3 g 1,3-dipalmitoyl-glycero-2-phosphate [Biochim.Biophys. Acta 553, 476 (1979) ], 2.6 g D,L-carnitine benzyl ester chloride [Lipids 10, 20 (1975) ] and 3.9 g 2,4,6-tri-isopropylbenzene sulphonyl chloride (TPS) as a condensing agent, are taken up in 250 ml anhydrous pyridine. After heating for 1 hour at 60° C. under stirring, the mixture is left for about 3 hours at room temperature. The mixture gets dark during the heating. Pyridine is evaporated under vacuum, and the residue is dried for 10 minutes under vacuum. After adding ethyl ether, the suspension is filtered. The ether solution is evaporated and the residue taken up in the smallest amount of chloroform and charged in a chromatographic column with 200 g silica gel (Merck 100).

The column, conditioned only with chloroform, is eluted with a methanol-water gradient. The purification is selective: with a 60:40:4 mixture only the interesting phospholipid is eluted.

The purified fraction weighs 2.5 g.

The residue is dissolved directly in 250 ml glacial acetic acid and 2.5 g 10% palladium on carbon are added. The hydrogenation proceeds very rapidly. After filtration on celite and washing with a $CH_3COOH/CHCl_3$ 1:1 mixture, the solution is evaporated at 10° C. maximum, under reduced pressure and the residue, well dried, is taken up in chloroform and precipitated with acetone, obtaining 1,3-dipalmitoyl-glycero-2-phospho-D,L-carnitine. Thin layer chromatography gives the following results:

$CHCl_3$: $CH_3OH$: $H_2O$ (60:30:4); Rf=0.07 .

$CHCl_3$: $CH_3OH$: $CH_3COOH$: $H_2O$ (25:15:4:2); Rf=0.57.

EXAMPLE 2

1,3-dipalmitoyl-glycero-2-phospho-L-carnitine 3 g 1,3-dipalmitoyl-glycero-2-phosphate [Biochim.Biopyys Acta 553, 476 (1979) ], 6 g L-carnitine benzyl ester tetraphenyl borate and 3.9 g 2,4,6-tri-isopropyl-benzene sulphony chloride (TPS) as a condensing agent, are taken up in 250 ml anhydrous pyridine. After heating for 1 hour at 60° C. under stirring, the mixture is left for about 3 hours at room temperature.

The mixture gets dark during the heating. Pyridine is evaporated under vacuum, and the residue is dried for 10 minutes under vacuum. After adding ethyl ether, the suspension is filtered. The ether solution is evaporated and the residue taken up in the smallest amount of chloroform and charged in a chromatographic column with 200 g silica gel (Merck 100).

The column, conditioned only with chloroform, is eluted with a methanol-water gradient. The purification is selective: with a 60:40:4 mixture only the interesting is eluted.

The purified fraction weighs 2.5 g.

The residue is dissolved directly in 250 ml glacial acetic acid and 2.5 g 10% palladium on carbon are added. The hydrogenation proceeds very rapidly. After filtration on celite and washing with a $CH_3COOH/CHCl_3$ 1:1 mixture, the solution is evaporated at 10° C. maximum, under vacuum and the residue, well dried, is taken up in chloroform and precipitated with acetone, obtaining 1,3-dipalmitoyl-glycero-2-phospho-L-carnitine. Thin layer chromatography gives the following results:

$CHCl_3$: $CH_3OH$: $H_2O$ (60:30:4); Rf=0.07.
$CHCl_3$: $CH_3OH$: $CH_3COOH$: $H_2O$ (25:15:4:2); Rf=0.57.

EXAMPLE 3

1,3-dimyristoyl-glycero-2-phospho-D,L-carnitine 8 g 1,3-dimirystoyl-glycero-2-phosphate [Biochim.Biophys. Acta 553, 476 (1979)], 7.7 g D,L-carnitine benzyl ester chloride [Lipids 10, 20 (1975)] and 12.2 g 2,4,6-tri-isopropylbenzene sulphonyly chloride (TPS) as a condensing agent, are taken up in 400 ml anhydrous pyridine. After heating for 1 hour at 60° C. under stirring, the mixture is left for about 3 hours at room temperature.

The mixture gets dark during the heating. Pyridine is evaporated under vacuum, and the residue is dried for 10 minutes under vacuum. After adding ethyl ether, the suspension is filtered. The ether solution is evaporated and the residue taken up in the smallest amount of chloroform and charged in a chromatographic column with 300 g silica gel (Merck 100).

The column, conditioned only with chloroform, is eluted with a methanol-water gradient. The purification is selective: with a 60:40:4 mixture only the interested phospholipid is eluted.

The purified fraction weighs 5.3 g.

The residue is dissolved directly in 300 ml glacial acetic acid and 4.0 g 10% palladium on carbon are added. The hydrogenation proceeds very rapidly. After filtration on celite and washing with a $CH_3COOH/CHCl_3$ 1:1 mixture, the solution is evaporated at 10° C. maximum, under vacuum and the residue, well dried, is taken up in chloroform and precipitated with acetone, obtaining 1,3-dimyristoyl-glycero-2-phospho-D,L-carnitine. Thin layer chromatography gives the following results:

$CHCl_3$: $CH_3OH$: $H_2O$ (60:30:4); Rf=0.07.
$CHCl_3$: $CH_3OH$: $CH_3COOH$: $H_2O$ (25:15:4:2); Rf=0.52.

EXAMPLE 4

1,3-dimyristoyl-glycero-2-phospho-L-carnitine 8 g 1,3-dimyristoyl-glycero-2-phosphate [Biochim.-Biophys. Acta 553, 476 (1979)], 17.5 g L-carnitine benzyl ester tetraphenylborate and 12.2 g 2,4,6-tri-isopropylbenzene sulphonyl chloride (TPS) as a condensing agent, are taken up in 400 ml anhydrous pyridine. After heating for 1 hour at 60° C. under stirring, the mixture is left for about 3 hours at room temperature.

The mixture gets dark during the heating. Pyridine is evaporated under vacuum, and the residue is dried for 10 minutes under vacuum. After adding ethyl ether, the suspension is filtered. The ether solution is evaporated and the residue taken up in the smallest amount of chloroform and charged in a chromatographic column with 300 g silica gel (Merck 100).

The column, conditioned only with chloroform, is eluted with a methanol-water gradient. The purification is selective: with a 60:40:4 mixture only the interested phospholipid is eluted.

The purified fraction weighs 4.3 g.

The residue is dissolved directly in 300 ml glacial acetic acid and 3 g 10% palladium on carbon are added. The hydrogenation proceeds very rapidly. After filtration on celite and washing with a $CH_3COOH/CHCl_3$ 1:1 mixture, the solution is evaporated at 10° C. maximum, under vacuum and the residue, well dried, is taken up in chloroform and precipitated with acetone, obtaining 1,3-dimyristoyl-glycero-2-phospho-L-carnitine. Thin layer chromatography gives the following results:

$CHCl_3$: $CH_3OH$: $H_2O$ (60:30:4); Rf=0.07.
$CHCl_3$: $CH_3OH$: $CH_3COOH$: $H_2O$ (25:15:4:2); Rf=0.52.

EXAMPLE 5

1,3-distearoyl-glycero-2-phospho-D,L-carnitine 8 g 1,3-distearoyl-glycero-2-phosphate [Biochim.Biophys. Acta 553, 476 (1979)], 6.8 g D,L-carnitine benzyl ester chloride [Lipids 10, 20 (1975)] and 10.7 g 2,4,6-tri-isopropylbenzene sulphonylchloride (TPS) as a condensing agent, are taken up in 400 ml anhydrous pyridine. After heating for 1 hour at 60° C. under stirring, the mixture is left for about 3 hours at room temperature.

The mixture gets dark during the heating. Pyridine is evaporated under vacuum, and the residue is dried for 10 minutes under vacuum. After adding ethyl ether, the suspension is filtered. The ether solution is evaporated and the residue taken up in the smallest amount of chloroform and charged in a chromatographic column with 300 g silica gel (Merck 100).

The column, conditioned only with chloroform, is eluted with a methanol-water gradient. The purification is selective: with a 60:40:4 mixture only the interested phospholipid is eluted.

The purified fraction weighs 8.0 g.

The residue is dissolved directly in 350 ml glacial acetic acid and 5.5 g 10% palladium on carbon are added. The hydrogenation proceeds very rapidly. After filtration on celite and washing with a $CH_3COOH/CHCl_3$ 1:1 mixture, the solution is evaporated at 10° C. maximum, under reduced pressure and the residue, well dried, is taken up in chloroform and precipitated with acetone, obtaining 1,3-distearoyl-glycero-2-phospho-D,L-carnitine. Thin layer chromatography gives the following results:

$CHCl_3$: $CH_3OH$: $H_2O$ (60:30:4); Rf=0.07.
$CHCl_3$: $CH_3OH$: $CH_3COOH$: $H_2O$ (25:15:4:2); Rf=0.59.

EXAMPLE 6

1,3-distearoyl-glycero-2-phospho-L-carnitine 8 g 1,3-distearoyl-glycero-2-phosphate [Biochim.Biophys. Acta 553, 476 (1979)], 15.3 g L-carnitine benzyl ester tetraphenyl borate and 10.7 g 2,4,6-tri-isopropylbenzene sulphonyl chloride (TPS) as a condensing agent, are taken up in 400 ml anhydrous pyridine.

After heating for 1 hour at 60° C. under stirring, the mixture is left for about 3 hours at room temperature.

The mixture gets dark during the heating. Pyridine is evaporated under vacuum, and the residue is dried for 10 minutes under vacuum. After adding ethyl ether, the suspension is filtered. The ether solution is evaporated and the residue taken up in the smallest amount of chloroform and charged in a chromatographic column with 300 g silica gel (Merck 100).

The column, conditioned only with chloroform, is eluted with a methanol-water gradient. The purification is selective: with a 60:40:4 mixture only the interested phospholipid is eluted.

The purified fraction weighs 6.1 g.

The residue is dissolved directly in 300 ml glacial acetic acid and 4.0 g 10% palladium on carbon are added. The hydrogenation proceeds very rapidly. After filtration on celite and washing with a $CH_3COOH/CHCl_3$ 1:1 mixture, the solution is evaporated at 10° C. maximum, under reduced pressure and the residue, well dried, is taken up in chloroform and precipitated with acetone, obtaining 1,3-distearoyl-glycero-2-phospho-L-carnitine. Thin layer chromatography gives the following results:

$CHCl_3$: $CH_3OH$: $H_2O$ (60:30:4); Rf=0.1.
$CHCl_3$: $CH_3OH$: $CH_3COOH$: $H_2O$ (25:15:4:2); Rf=0.59.

EXAMPLE 7

1-myristoyl-2-deoxyglycero-3-Phospho-D,L-Carnitine a) 24.4 g phosphor oxychloride are added to 300 ml THF. The solution is cooled to −10° C. and a solution of 19.3 g pyridine in 400 mi THF is added slowly under stirring.

To the resulting mixture, kept always at −10° C., a solution of 35 g monomyristoyl-1,3propandiol in 700 ml THF is added very slowly under stirring.

Once the addition is terminated, the mixture is brought to 40° C. for one hour and is then concentrated to half its original volume; the precipitate that forms is filtered off. The resulting solution is cooled to −5° C. and then 1000 ml of a 5% sodium bicarbonate solution are added slowly under stirring.

The mixture is then brought to room temperature for one hour, after which 400 ml chloroform are added; the addition of sodium chloride allows the extraction of the 1-myristoyl-2-deoxyglycero-3-phosphate in the chloroform phase.

The chloroform solution is dried on anhydrous sodium sulphate, filtered and concentrated. 40 g 1-myristoyl-2-deoxyglycero-3-phosphate are obtained.

Thin layer chromatography shows:

Eluent $CHCl_3$: $CH_3OH$: $H_2O$ (60:30:4); Rf: 0.43.

b) 6.0 g 1-myristoyl-2-deoglycero-3-phosphate, 9.4 g D,L-carnitine benzyl ester tetraphenylborate and 9.9 g 2,4,6-triisopropyl benzene sulphonyl chloride (TPS) as condensing agent are taken up in 300 ml anhydrous pyridine. After heating to 40° C. for 15 minutes under stirring, the solution is left at room temperature for about 5 hours.

Pyridine is evaporated under vacuum and the residue is taken up in ethyl ether; the suspension obtained is filtered.

The ether solution is evaporated and the residue taken up in a small amount of chloroform and charged in a 500 g silica gel (Merck 100) chromatographic column.

The column conditioned with chloroform is eluted with a methanol-water gradient.

The product exit takes place with a 60:30:5 chloroform/methanol/water mixture.

The purified fraction amounts to 6.5 g.

The residue is dissolved directly in 400 mi glacial acetic acid and 4.0 g 10% palladium on carbon are added. The hydrogenation is started, which progresses very rapidly.

After filtration on Celite and washing with a 1:1 $CH_3COOH/CHCl_3$ mixture, the -solution is evaporated at maximum 40° C. under vacuum, the residue, thoroughly dried, is taken up in chloroform and precipitated with acetone, 1-myristoyl-2-deoxyglycero-3-phospho-D,L-carnitine is obtained.

Thin layer chromatography gives the following results:

eluent $CHCl_3$: $CH_3OH$: $H_2O$ (60:30:4); Rf: 0.06.
$CHCl_3$: $CH_3OH$: $CH_3COOH$: $H_2O$ (25:15:4:2); Rf: 0.25.

EXAMPLE 8

1-Myristoyl-2-deoxyglycero-3-Phospho-L-Carnitine a) This step is carried out in the same manner as in Example 7.

b) 6.0 g 1-myristoyl-2-deoxyglycero-3-phosphate, 9.4 g L-carnitine benzyl ester tetraphenylborate and 9.9 g 2,4,6-triisopropyl benzene sulphonyl chloride (TPS) as condensing agent are taken up in 300 ml anhydrous pyridine. After heating to 40° C. for 15 minutes under stirring, the solution is left at room temperature for about 5 hours.

Pyridine is evaporated under vacuum and the residue is taken up in ethyl ether; the suspension obtained is filtered.

The ether solution is evaporated and the residue taken up in a small amount of chloroform and charged in a 500 g silica gel (Merck 100) chromatographic column.

The column conditioned with chloroform is eluted with a methanol-water gradient.

The product exit takes place with a 60:30:5 chloroform/methanol/water mixture.

The purified fraction amounts to 6.5 g.

The residue is dissolved directly in 400 mi glacial acetic acid and 4.0 g 10% palladium on carbon are added. The hydrogenation is started, which progresses very rapidly.

After filtration on Celite and washing with a 1:1 $CH_3COOH/CHCl_3$ mixture, the solution is evaporated at maximum 40° C. under vacuum, the residue, thoroughly dried, is taken up in chloroform and precipitated with acetone, 1-myristoyl-2-deoxyglycero-3-phospho-L-carnitine is obtained.

Thin layer chromatography gives the following results:

eluent $CHCl_3$: $CH_3OH$: $H_2O$ (60:30:4); Rf: 0.06.
$CHCl_3$: $CH_3OH$: $CH_3COOH$: $H_2O$ (25:15:4:2); Rf: 0.25.

EXAMPLE 9

1-Palmitoyl-2-deoxyglycero-3-Phospho-D,L-Carnitine a) 9.8 g phosphor oxychloride are added to 100 ml THF. The solution is cooled to −10° C. and a solution of 7.5 g pyridine in 150 ml THF is added slowly under stirring.

To the resulting mixture, kept always at −10° C., a solution of 15 g monopalmitoyl-1,3-propandiol in 280 mi THF is added very slowly under stirring.

Once the addition is terminated, the mixture is brought to 40° C. for one hour and is then concentrated to half its original volume; the precipitate that forms is filtered off. The resulting solution is cooled to −5° C.

and then 400 ml of a 5% sodium bicarbonate solution are added slowly under stirring.

The mixture is then brought to room temperature for one hour, after which 200 ml chloroform are added; the addition of sodium chloride allows the extraction of the 1-palmitoyl-2-deoxyglycero-3-phosphate in the chloroform phase.

The chloroform solution is dried on anhydrous sodium sulphate, filtered and concentrated. 16 g 1-palmitoyl-2-deoxyglycero-3-phosphate are obtained.

Thin layer chromatography shows:

Eluent $CHCl_3$: $CH_3OH$: $H_2O$ (60:30:4); Rf: 0.46.

b) 4 g 1-palmitoyl-2-deoxyglycero-3-phosphate, 6.1 g D,L-carnitine benzyl ester tetraphenylborate and 6.1 g 2,4,6-triisopropyl benzene sulphonyl chloride (TPS) as condensing agent are taken up in 160 ml anhydrous pyridine. After heating to 40° C. for 15 minutes under stirring, the solution is left at room temperature for about 5 hours.

Pyridine is evaporated under vacuum and the residue is taken up in ethyl ether; the suspension obtained is filtered.

The ether solution is evaporated and the residue taken up in a small amount of chloroform and charged in a 280 g silica gel (Merck 100) chromatographic column.

The column conditioned with chloroform is eluted with a methanol-water gradient.

The product exit takes place with a 60:30:5 chloroform/methanol/water mixture.

The purified fraction amounts to 3.5 g.

The residue is dissolved directly in 200 ml glacial acetic acid and 2.0 g 10% palladium on carbon are added. The hydrogenation is started, which progresses very rapidly.

After filtration on Celite and washing with a 1:1 $CH_3COOH/CHCl_3$ mixture, the solution is evaporated at maximum 40° C. under vacuum, the residue, thoroughly dried, is taken up in chloroform and precipitated with acetone, 1-palmitoyl-2-deoxyglycero-3-phospho-D,L-carnitine is obtained.

Thin layer chromatography gives the following results:

eluent $CHCl_3$: $CH_3OH$: $H_2O$ (60:30:4); Rf: 0.06.

$CHCl_3$: $CH_3OH$: $CH_3COOH$: $H_2O$ (25:15:4:2); Rf: 0.27.

EXAMPLE 10

1-Palmitoyl-2-deoxyglycero-3-Phospho-L-Carnitine a) This step is carried out in the same manner as in Example 9.

b) 4 g 1-palmitoyl-2-deoxyglycero-3-phosphate, 6.1 g L-carnitine benzyl ester tetraphenylborate and 6.1 g 2,4,6-triisopropyl benzene sulphonyl chloride (TPS) as condensing agent are taken up in 160 ml anhydrous pyridine. After heating to 40° C. for 15 minutes under stirring, the solution is left at room temperature for about 5 hours.

Pyridine is evaporated under vacuum and the residue is taken up in ethyl ether; the suspension obtained is filtered.

The ether solution is evaporated and the residue taken up in a small amount of chloroform and charged in a 280 g silica gel (Merck 100) chromatographic column.

The column conditioned with chloroform is eluted with a methanol-water gradient.

The product exit takes place with a 60:30:5 chloroform/methanol/water mixture.

The purified fraction amounts to 3.5 g.

The residue is dissolved directly in 200 ml glacial acetic acid and 2.0 g 10% palladium on carbon are added. The hydrogenation is started, which progresses very rapidly.

After filtration on Celite and washing with a 1:1 $CH_3COOH/CHCl_3$ mixture, the solution is evaporated at maximum 40° C. under vacuum, the residue, thoroughly dried, is taken up in chloroform and precipitated with acetone, 1-palmitoyl-2-deoxyglycero-3-phospho-L-carnitine is obtained.

Thin layer chromatography gives the following results:

eluent $CHCl_3$: $CH_3OH$: $H_2O$ (60:30:4); Rf: 0.06.

$CHCl_3$: $CH_3OH$: $CH_3COOH$: $H_2O$ (25:15:4:2); Rf: 0.27.

EXAMPLE 11

1-Stearoyl-2-deoxyglycero-3-Phospho-D,L-Carnitine a) 11.9 g phosphor oxychloride are added to 100 ml THF. The solution is cooled to $-10°$ C. and a solution of 9.2 g pyridine in 180 ml THF is added slowly under stirring.

To the resulting mixture, kept always at $-10°$ C., a solution of 20 g monostearoyl-1,3-propandiol in 380 ml THF is added very slowly under stirring.

Once the addition is terminated, the mixture is brought to 40° C. for one hour and is then concentrated to half its original volume; the precipitate that forms is filtered off. The resulting solution is cooled to $-5°$ C. and then 600 ml of a 5% sodium bicarbonate solution are added slowly under stirring.

The mixture is then brought to room temperature for one hour, after which 200 ml chloroform are added; the addition of sodium chloride allows the extraction of the 1-stearoyl-2-deoxyglycero-3-phosphate in the chloroform phase.

The chloroform solution is dried on anhydrous sodium sulphate, filtered and concentrated. 21 g 1-stearoyl-2-deoxyglycero-3-phosphate are obtained.

Thin layer chromatography shows:

Eluent $CHCl_3$: $CH_3OH$: $H_2O$ (60:30:4); Rf: 0.47.

b) 6.0 g 1-stearoyl-2-deoxyglycero-3-phosphate, 8.3 g D,L-carnitine benzyl ester tetraphenylborate and 8.6 g 2,4,6-triisopropyl benzene sulphonyl chloride (TPS) as condensing agent are taken up in 250 ml anhydrous pyridine. After heating to 40° C. for 15 minutes under stirring, the solution is left at room temperature for about 5 hours.

Pyridine is evaporated under vacuum and the residue is taken up in ethyl ether; the suspension obtained is filtered.

The ether solution is evaporated and the residue taken up in a small amount of chloroform and charged in a 500 g silica gel (Merck 100) chromatographic column.

The column conditioned with chloroform is eluted with a methanol-water gradient.

The product exit takes place with a 60:30:5 chloroform/methanol/water mixture.

The purified fraction amounts to 7.2 g.

The residue is dissolved directly in 400 ml glacial acetic acid and 4.0 g 10% palladium on carbon are added. The hydrogenation is started, which progresses very rapidly.

After filtration on Celite and washing with a 1:1 $CH_3COOH/CHCl_3$ mixture, the solution is evaporated at maximum 40° C. under vacuum, the residue, thoroughly dried, is taken up in chloroform and precipitated with acetone, 1-stearoyl-2-deoxyglycero-3-phospho-D,L-carnitine is obtained.

Thin layer chromatography gives the following results:

eluent $CHCl_3$: $CH_3OH$: $H_2O$ (60:30:4); Rf: 0.07.
$CHCl_3$: $CH_3OH$: $CH_3COOH$: $H_2O$ (25:15:4:2).

EXAMPLE 12

1-Stearoyl-2-deoxyglycero-3-Phospho-L-Carnitine a) This step is carried out in the same manner as in Example 11.

b) 6.0 g 1-stearoyl-2-deoxyglycero-3-phosphate, 8.3 g L-carnitine benzyl ester tetraphenylborate and 8.6 g 2,4,6-triisopropyl benzene sulphonyl chloride (TPS) as condensing agent are taken up in 250 ml anhydrous pyridine. After heating to 40° C. for 15 minutes under stirring, the solution is left at room temperature for about 5 hours.

Pyridine is evaporated under vacuum and the residue is taken up in ethyl ether; the suspension obtained is filtered.

The ether solution is evaporated and the residue taken up in a small amount of chloroform and charged in a 500 g silica gel (Merck 100) chromatographic column.

The column conditioned with chloroform is eluted with a methanol-water gradient.

The product exit takes place with a 60:30:5 chloroform/methanol/water mixture.

The purified fraction amounts to 7.2 g.

The residue is dissolved directly in 400 ml glacial acetic acid and 4.0 g 10% palladium on carbon are added. The hydrogenation is started, which progresses very rapidly.

After filtration on Celite and washing with a 1:1 $CH_3COOH/CHCl_3$ mixture, the solution is evaporated at maximum 40° C. under vacuum. The residue, thoroughly dried, is taken up in chloroform and precipitated with acetone, 1-stearoyl-2-deoxyglycero-3-phospho-L-carnitine is obtained.

Thin layer chromatography gives the following results:

eluent $CHCl_3$: $CH_3OH$: $H_2O$ (60:30:4); Rf: 0.07.
$CHCl_3$: $CH_3OH$: $CH_3COOH$: $H_2O$ (25:15:4:2); Rf: 0.29.

EXAMPLE 13

1,3-dimyristoylglycero-2-phospho-L-carnitine a) 55.7 g imidazole are dissolved in 500 ml hot toluene. Toluene is evaporated and the residue, taken up with 500 ml methylene chloride, is transferred in a 2000 ml reaction vessel fitted with a stirrer. After cooling to −15° C., 32.1 g phosphor trichloride dissolved in 350 ml methylene chloride are added. 47.3 g triethylamine in 350 ml methylene chloride are then added, and, after 10 minutes, 30 g 1,3-dimyristoylglycerol dissolved in 500 ml methylene chloride.

Once the addition is terminated, the temperature is brought to −5° C. and after 1 hour to room temperature. After further 30 minutes, the solvent is evaporated, the residue is taken up in 100 ml acetone, the solution is cooled to −5° C. and, under stirring, 1200 ml of a 59 sodium bicarbonate water solution are added.

After 1 hour the precipitate is filtered and washed twice with 500 ml water and twice with 500 ml acetone. After a further washing with 500 ml warm ethyl ether, 31 g 1,3-dimyristoylglycero-2-H-phosphonate are obtained.

Thin layer chromatography: chloroform/methanol/water eluent (60:30:4); Rf: 0.58.

b) 30 g 1,3-dimyristoylglycero-2-H-phosphonate and 16.8 g L-carnitine are dissolved in 500 ml anhydrous pyridine. After concentration, the residue is taken up in 800 ml anhydrous pyridine, 28.8 g 5,5-dimethyl-2-oxo-2-chloro-1,3,2-dioxo-phosphorinane (McConnell R.L., Coover H.W., J. Org. Chem., 1959, 24, 630–635) and the reaction is carried out at 40° C., under continuous stirring for 30 minutes.

Pyridine is evaporated and the residue is dried under high vacuum. The dried residue is taken up in 1000 ml ethyl ether under stirring for 30 minutes, then the salt is filtered out and the solution is concentrated.

400 ml pyridine are added and then 10 ml water and 26.4 g iodine; after stirring for 15 minutes, 1000 ml chloroform and 1000 ml 5% sodium bisulphite water solution are added.

After separation, the washing is repeated with 500 ml chloroform. Chloroform is dried and concentrated. The residue is taken up in 1000 ml acetone, 160 ml 1M water solution of sodium acetate are added. and, after 1 hour stirring at −15° C. is filtered and dried under high vacuum. 30 g 1,3-dimyristoylglycero-2-phospho-L-carnitine are obtained.

Thin layer chromatography: chloroform/methanol/water (60:30:4) eluent, Rf: 0.07; chloroform/methanol/acetic acid/water (25:15:4:2), Rf:0.52.

EXAMPLE 14

1,3-dipalmitoylglycero-2-phospho-L-carnitine a) 50.5 g imidazole are dissolved in 450 ml hot toluene. Toluene is evaporated and the residue, taken up with 450 ml methylene chloride, is transferred in a 2000 ml reaction vessel fitted with a stirrer.

After cooling to −15° C., 29.1 g phosphor trichloride dissolved in 350 ml methylene chloride are added. 42.9 g triethylamine in 350 ml methylene chloride are then added, and, after 10 minutes, 30 g 1,3-dipalmitoylglycerol dissolved in 600 ml methylene chloride.

Once the addition is terminated, the temperature is brought to −5° C. and after 1 hour to room temperature. After further 30 minutes, the solvent is evaporated, the residue is taken up in 100 ml acetone, the solution is cooled to −5° C. and, under stirring, 1000 ml of a 5% sodium bicarbonate water solution are added.

After 1 hour the precipitate is filtered and washed twice with 500 ml water and twice with 500 ml acetone. After a further washing with 500 ml warm ethyl ether, 32 g 1,3-dipalmitoylglycero-2-H-phosphonate are obtained.

Thin layer chromatography: chloroform/methanol/water eluent (60:30:4); Rf: 0.60.

b) 30 g 1,3-dipalmitoylglycero-2-H-phosphonate and 15.1 g L-carnitine are dissolved in 500 ml anhydrous pyridine. After concentration, the residue is taken up in 800 ml anhydrous pyridine, 26 g 5,5-dimethyl-2-oxo-2-chloro-1,3,2-dioxo-phosphorinane (McConnell R.L., Coover H.W., J. Org. Chem., 1959, 24, 630–635) and the reaction is carried out at 40° C., under continuous stirring for 30 minutes.

Pyridine is evaporated and the residue is dried under high vacuum for 30 minutes. The dried residue is taken up in 1000 ml ethyl ether under stirring for 30 minutes, then the salt is filtered out and the solution is concentrated.

400 ml pyridine are added and then 10 ml water and 23.8 g iodine; after stirring for 15 minutes, 1000 ml chloroform and 900 ml 5% sodium bisulphite water solution are added.

After separation, the washing is repeated with 500 ml chloroform. Chloroform is dried and concentrated. The residue is taken up in 1000 ml acetone, 150 ml 1M water solution of sodium acetate are added, and, after 1 hour stirring at −15° C. is filtered and dried under high vacuum. 32 g 1,3-dipalmitoylglycero-2-phospho-L-carnitine are obtained.

Thin layer chromatography: chloroform/methanol/water (60:30:4) eluent, Rf: 0.07; chloroform/methanol/acetic acid/water (25:15:4:2), Rf:0.57.

EXAMPLE 15

1.3-distearoylglycero-2-phospho-L-carnitine a) 45.8 g imidazole are dissolved in 400 ml hot toluene. Toluene is evaporated and the residue, taken up with 400 ml methylene chloride, is transferred in a 2000 ml reaction vessel fitted with a stirrer. After cooling to −15° C., 19.8 g phosphor trichloride dissolved in 300 ml methylene chloride are added. 38.9 g triethylamine in 300 ml methylene chloride are then added, and, after 10 minutes, 30 g 1,3-distearoylglycerol dissolved in 500 ml methylene chloride.

Once the addition is terminated, the temperature is brought to −5° C. and after 1 hour to room temperature. After further 30 minutes, the solvent is evaporated, the residue is taken up in 100 ml acetone, the solution is cooled to −5° C. and, under stirring, 800 ml of a 5% sodium bicarbonate water solution are added.

After 1 hour the precipitate is filtered and washed twice with 500 ml water and twice with 500 ml acetone. After a further washing with 500 ml warm ethyl ether, 31 g 1,3-distearoylglycero-2-H-phosphonate are obtained.

Thin layer chromatography: chloroform/methanol/water eluent (60:30:4); Rf: 0.61.

b) 30 g 1,3-distearoylglycero-2-H-phosphonate and 13.7 g L-carnitine are dissolved in 500 ml anhydrous pyridine. After concentration, the residue is taken up in 800 ml anhydrous pyridine, 23.8 g 5,5-dimethyl-2-oxo-2-chloro-1,3,2-dioxo-phosphorinane (McConnell R.L., Coover H.W., J. Org. Chem., 1959, 24, 630–635) and the reaction is carried out at 40° C., under continuous stirring for 30 minutes.

Pyridine is evaporated and the residue is dried under high vacuum for 30 minutes. The dried residue is taken up in 1000 ml ethyl ether under stirring for 30 minutes, then the salt is filtered out and the solution is concentrated.

400 ml pyridine are added and then 10 ml water and 21.8 g iodine; after stirring for 15 minutes, 1000 ml chloroform and 850 ml 5% sodium bisulphite water solution are added.

After separation, the washing is repeated with 500 ml chloroform. Chloroform is dried and concentrated. The residue is taken up in 1000 ml acetone, 130 ml 1M water solution of sodium acetate are added, and, after 1 hour stirring at −15° C. is filtered and dried under high vacuum. 31 g 1,3-distearoylglycero-2-phospho-L-carnitine are obtained.

Thin layer chromatography: chloroform/methanol/water (60:30:4) eluent, Rf: 0.07; chloroform/methanol/acetic acid/water (25:15:4:2), Rf: 0.59.

The new derivatives according to the present invention are active in the therapy of human diseases associated with neuronal damages.

More particularly, the new carnitine derivatives are effective in the therapy of peripheral neuropathies, of cerebrovascular affections and of cerebral level traumas of cerebral aging and of chronic neurodegenerative affections.

Examples of human diseases associated with neuronal damages, both morphologic and functional, are the following:

a. Damage of traumatic, metabolic or toxic origin of the peripheral nervous system (peripheral neuropathies).

b. Damage of traumatic or vascular origin of the cerebral nervous system (neurovascular diseases and traumas at cerebral level).

c. Damage associated with aging of the central nervous system (cerebral aging).

d. Damage due to still unknown etiopathologic causes (chronic neurodegenerative diseases) or infectious or tumoral diseases. As peripheral neuropathies we intend a group of permanent peripheral nerve disorders which may take place separately or more often as part of more complex pathologies.

A pathological classification of peripheral neuropathies was suggested by P.K. Thomas—International Conference on Peripheral Neuropathies, 24th-25th Jun. 1981, Madrid p-79, Excerpta Medica, as reported in Table I.

TABLE I

| Pathological Classification of Peripheral Neuropathies | |
|---|---|
| 1. | Disorders generally leading to axon loss |
| | a. Neurophaties |
| | Spinal muscolar atrophy |
| | Degeneration of dorsal root cells |
| | and autonomous ganglions |
| | cells |
| | b. Axonopathies |
| | Proximal axonopathy |
| | Distal axonopathy |
| | Focal axonal interruption |
| 2. | Disorders essentially concerning supporting tissues |
| | Disorders of Schwann cells |
| | Myelinopathies |
| | Disorders of the neural connective tissue |
| | Vascular disturbances |

A general separation may be made between disorders which essentially produce axone loss in peripheral nerves and those in which the nervous fibre lesion is secondary to disturbances concerning the supporting structures, including Schwann cells and myelin, connective nervous tissues and the vascular system.

The first category of disturbaces may be further subdivided between conditions in which complete loss of the neuron takes place (neuropathies) and the ones in which a selective axone destruction takes place.

The same author suggests a peripheral neuropathy classification on etiologic basis, as reported in Table II.

TABLE II

| Etiologic Classification of Peripheral Neuropathies |
|---|
| Neuropathies due to: |

| Etiologic Classification of Peripheral Neuropathies |
| --- |
| Physical agents |
| associated to systemic diseases |
| toxic neuropathies |
| nutritional deficiencies |
| inflammations and postinfection disorders |
| neuroplasias and paraproteinemias |
| hereditary factors |
| cryptogenic factors |

The pharmaceutical compositions having an activity in the therapy of peripheral neuropathies and containing new carnitine derivatives according to the present invention, contain an amount of active principle comprised between 100 and 1000 mg, preferably between 200 and 500 mg, and may be prepared in a form suitable for oral or parenteral administration according to the formulations normally employed in the pharmaceutical technology.

The therapeutic method for the therapy of human pathologies due to neuronal damages, characterized by the administration of a therapeutically effective amount of phosphatidyl carnitine derivatives, or of their pharmacologically acceptable salts of general formula (I) is effected by administration, per os or parenteral, of an amount of active principle comprised between 10 and 80 mg/kg/day, preferably between 20 and 50 mg/kg/day in from 2 to 4 administration/day.

We list hereinbelow, for purely illustrative and not limitative purpose, some examples of practical embodiments of pharmaceutical compositions according to the present invention.

| Injectable pharmaceutical compositions | | |
| --- | --- | --- |
| Example 1 | | |
| A 2 ml vial contains: | | |
| 1,3-dipalmitoyl-glycero-2-phosphoryl-L-carnitine | | mg 200 |
| monobasic sodium phosphate | | mg 2.4 |
| bibasic sodium phosphate | | mg 2.26 |
| bidistilled apyrogenic water | q.s. to | ml 2 |
| Example 2 | | |
| A 2 ml vial contains: | | |
| 1,3-dipivaloyl-glycero-2-phosphoryl-L-carnitine | | mg 200 |
| monobasic sodium phosphate | | mg 2.4 |
| bibasic sodium phosphate | | mg 2.26 |
| bidistilled apyrogenic water | q.s. to | ml 2 |
| Example 3 | | |
| A 2 ml vial contains: | | |
| 1,3-dimyristoyl-glycero-2-phosphoryl-L-carnitine | | mg 200 |
| monobasic sodium phosphate | | mg 2.4 |
| bibasic sodium phosphate | | mg 2.26 |
| bidistilled apyrogenic water | q.s. to | ml 2 |
| Example 4 | | |
| A ml 3 vial contains: | | |
| 1,3-dipalmitoyl-glycero-2-phosphoryl-L-carnitine | | mg 300 |
| monobasic sodium phosphate | | mg 3.21 |
| bibasic sodium phosphate | | mg 3.39 |
| mannitol | | mg 30 |
| bidistilled apyrogenic water | q.s. to | ml 3 |
| Example 5 | | |
| A ml 3 vial contains: | | |
| 1,3-dipivaloyl-glycero-2-phosphoryl-L-carnitine | | mg 300 |
| monobasic sodium phosphate | | mg 3.21 |
| bibasic sodium phosphate | | mg 3.39 |
| mannitol | | mg 30 |
| bidistilled apyrogenic water | q.s. to | ml 3 |
| Example 6 | | |
| A ml 3 vial contains: | | |
| 1,3-dimyristoyl-glycero-phosphoryl-L-carnitine | | mg 300 |
| monobasic sodium phosphate | | mg 3.21 |
| bibasic sodium phosphate | | mg 3.39 |
| mannitol | | mg 30 |
| bidistilled apyrogenic water | q.s. to | ml 3 |

| Oral pharmaceutical compositions | |
| --- | --- |
| Example 7 | |
| A gelatine capsule contains: | |
| 1,3-dipalmitoyl-glycero-2-phosphoryl-L-carnitine | mg 400 |
| vegetable oil | mg 270 |
| bee wax | mg 1 |
| Example 8 | |
| A gelatine capsule contains: | |
| 1,3-dipivaloyl-glycero-2-phosphoryl-L-carnitine | mg 400 |
| vegetable oil | mg 270 |
| bee wax | mg 1 |
| Example 9 | |
| A gelatine capsule contains: | |
| 1,3-dimyristoyl-glycero-2-phosphoryl-L-carnitine | mg 400 |
| vegetable oil | mg 270 |
| bee wax | mg 1 |
| Example 10 | |
| A gelatine capsule contains: | |
| 1,3-dipalmitoyl-glycero-2-phosphoryl-L-carnitine | mg 500 |
| vegetable oil | mg 270 |
| bee wax | mg 1 |
| Example 11 | |
| A gelatine capsule contains: | |
| 1,3-dipivaloyl-glycero-2-phosphoryl-L-carnitine | mg 500 |
| vegetable oil | mg 270 |
| bee wax | mg 1 |
| Example 12 | |
| A gelatine capsule contains: | |
| 1,3-dimyristoyl-glycero-2-phosphoryl-L-carnitine | mg 500 |
| vegetable oil | mg 270 |
| bee wax | mg 1 |
| Example 13 | |
| A dragee contains: | |
| 1,3-dipalmitoyl-glycero-2-phosphoryl-L-carnitine | mg 250 |
| mannitol | mg 100 |
| microcrystalline cellulose | mg 25 |
| starch | mg 5 |
| sucrose | mg 30 |
| lacquer | mg 5 |
| Example 14 | |
| A dragee contains: | |
| 1,3-dipivaloyl-glycero-2-phosphoryl-L-carnitine | mg 250 |
| mannitol | mg 100 |
| microcrystalline cellulose | mg 25 |
| starch | mg 5 |
| sucrose | mg 30 |

-continued

| Oral pharmaceutical compositions | | |
|---|---|---|
| lacquer | mg | 5 |
| Example 15 | | |
| A dragee contains: | | |
| 1,3-dimyristoyl-glycero-2-phosphoryl-L-carnitine | mg | 250 |
| mannitol | mg | 100 |
| microcrystalline cellulose | mg | 25 |
| starch | mg | 5 |
| sucrose | mg | 30 |
| lacquer | mg | 5 |
| Example 16 | | |
| A cachet contains: | | |
| 1,3-dipalmitoyl-glycero-2-phosphoryl-L-carnitine | mg | 450 |
| mannitol | mg | 100 |
| lactose | mg | 10 |
| Example 17 | | |
| A cachet contains: | | |
| 1,3-dipivaloyl-glycero-2-phosphoryl-L-carnitine | mg | 450 |
| mannitol | mg | 100 |
| lactose | mg | 100 |
| Example 18 | | |
| A cachet contains: | | |
| 1,3-dimyristoyl-glycero-2-phosphoryl-L-carnitine | mg | 450 |
| mannitol | mg | 100 |
| lactose | mg | 100 |

We claim:

1. Carnitine derivatives of the formula (I)

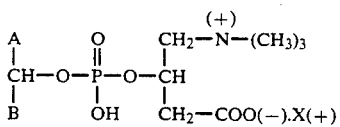

where A=—H or —(CH$_2$)$_m$—O—CO—R$_1$ wherein N=1 or 2, and B=—(CH$_2$)$_m$—O—CO—R$_2$ wherein m=1, 2, 3 or 4, with the limitation that when A=—(CH$_2$)$_n$—O—CO—R$_1$, m=1 or 2, and where R$_1$ and R$_2$, same or different, are monovalent radicals of saturated mono or polyunsaturated acids of the aliphatic series with a maximum of 20 carbon atoms, of bicarboxylic acids, of hydroxy or aminoacids, of aromatic acids selected from the group consisting of benzoyl group optionally substituted in the benzene ring, araliphatic acids, alicyclic acids or heterocyclic acids, X being an alkali or alkaline earth metal, a primary, secondary or tertiary amine cation or a quaternary ammonium, aliphatic, aromatic or heterocyclic base.

2. Carnitine derivatives according to claim 1, wherein R$_1$ and R$_2$ are radicals of pivalic, lauric, myristic, palmitic, palmitoleic stearic, linoleic, linolenic and arachidonic acids.

3. Carnitine derivatives of the formula (I)

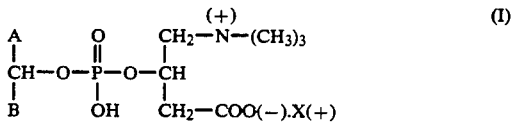

where A=—H or —(CH$_2$)$_n$—O—CO—R$_1$ wherein n=1 or 2, and B=—(CH$_2$)$_m$—O—CO—R$_2$ wherein m=1, 2, 3 or 4, with the limitation that when A=—(CH$_2$)$_n$—O—CO—R$_1$, m=1 or 2, and wherein R$_1$ and R$_2$ are radicals of benzoic acid optionally substituted in the benzene ring and x being an alkali or alkaline earth metal, a primary, secondary or tertiary amine or a quaternary ammonium, aliphatic, aromatic or heterocyclic base.

4. Pharmaceutical compositions containing as active principle at least one compound of the formula I'

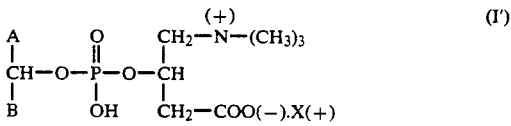

where A=—H or —(CH$_2$)$_n$—O—CO—R$_1$ wherein n=1 or 2, and B=—(CH$_2$)$_m$—O—CO—R$_2$ wherein m=1, 2, 3 or 4, with the limitation that when A=—(CH$_2$)$_n$—O—CO—R$_1$, m=1 or 2, and where R$_1$ and R$_2$, the same or different, are radicals of acids of the aliphatic, aromatic, araliphatic, alicyclic or heterocyclic series, X being an alkali or alkaline earth metal, a primary, secondary or tertiary amine or a quaternary ammonium, aliphatic, aromatic or heterocyclic base, which is active in the therapy of human pathologies associated with neuronal damages.

5. Therapeutic method for the treatment of human pathologies associated with neuronal damages, comprising the administration of an effective amount of a pharmaceutical composition comprising, as active principle, at least one compound of formula I' according to claim 4.

* * * * *

UNITED STATES PATENT AND TRADEMARK OFFICE
CERTIFICATE OF CORRECTION

PATENT NO. : 5,260,464
DATED : November 9, 1993
INVENTOR(S) : Della Valle, et. al.

It is certified that error appears in the above-indentified patent and that said Letters Patent is hereby corrected as shown below:

Title page, item [54], Title and col. 1, line 1, change "CARNITURE" to -- CARNITINE --.

Title page, item [75], inventor: line, 1, change "Padua" to --Padova--.

Signed and Sealed this

Nineteenth Day of July, 1994

Attest:

BRUCE LEHMAN

Attesting Officer     Commissioner of Patents and Trademarks